United States Patent
Sattler et al.

(10) Patent No.: US 11,136,279 B2
(45) Date of Patent: Oct. 5, 2021

(54) INTEGRATED PROCESS FOR PRODUCING OLEFINS FROM ALKANES BY HYDROGEN TRANSFER

(71) Applicant: ExxonMobil Research and Engineering Company, Annandale, NJ (US)

(72) Inventors: Aaron Sattler, Annandale, NJ (US); Michele Paccagnini, Randolph, NJ (US); Kun Wang, Bridgewater, NJ (US); Henry K. Klutse, Hillside, NJ (US); Brian M. Weiss, Bridgewater, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 16/935,399

(22) Filed: Jul. 22, 2020

(65) Prior Publication Data
US 2021/0087122 A1  Mar. 25, 2021

Related U.S. Application Data

(60) Provisional application No. 62/905,714, filed on Sep. 25, 2019.

(51) Int. Cl.
*C07C 5/52* (2006.01)
*C07C 5/32* (2006.01)
(Continued)

(52) U.S. Cl.
CPC .............. *C07C 5/52* (2013.01); *C07C 4/06* (2013.01); *C07C 5/325* (2013.01); *C07C 9/04* (2013.01);
(Continued)

(58) Field of Classification Search
CPC ......... C07C 5/325; C07C 5/3337; C07C 5/52; C07C 4/06; C07C 9/04; C07C 11/06; C07C 2523/62; C07C 2523/656; Y02P 20/10
See application file for complete search history.

(56) References Cited

U.S. PATENT DOCUMENTS 3,254,017 A * 5/1966 Arey, Jr. ................ C10G 65/10
                                                                 208/59
3,321,545 A   5/1967 Rigney et al.
(Continued)

OTHER PUBLICATIONS

Zimmerman et al. ("Ethylene" Ullmann's Encyclopedia of Industrial Chemistry. Published Apr. 15, 2009 https://doi.org/10.1002/14356007.a10_045.pub3) (Year: 2009).*
(Continued)

*Primary Examiner* — Youngsul Jeong
*Assistant Examiner* — Jason Y Chong
(74) *Attorney, Agent, or Firm* — Robert A. Migliorini

(57) ABSTRACT

This application relates to transfer hydrogenation between light alkanes and olefins, and, more particularly, embodiments related to an integrated olefin production system and process which can produce higher carbon number olefins from corresponding alkanes. Examples methods may include reacting at least a portion of the ethylene and the at least one alkane via transfer hydrogenation to produce at least a mixed product stream comprising generated ethane from at least a portion of the ethylene, unreacted ethylene, and an olefin corresponding to the at least one alkane.

13 Claims, 3 Drawing Sheets

(51) Int. Cl.
*C07C 4/06* (2006.01)
*C07C 9/04* (2006.01)
*C07C 11/06* (2006.01)

(52) U.S. Cl.
CPC .......... *C07C 11/06* (2013.01); *C07C 2523/62* (2013.01); *C07C 2523/656* (2013.01)

(56) References Cited

U.S. PATENT DOCUMENTS

| | | |
|---|---|---|
| 5,227,552 A | 7/1993 | Chang et al. |
| 5,461,182 A | 10/1995 | Hellring et al. |
| 5,585,530 A | 12/1996 | Gough et al. |
| 7,902,417 B2 | 3/2011 | Goldman et al. |

OTHER PUBLICATIONS

Michael C. Haibach et al., "Alkane Metathesis by Tandem Alkane-Dehydrogenation-Olefin-Metathesis Catalysis and Related Chemistry", Accounts of Chemical Research 2012, vol. 45(6), pp. 947-958.

Alan S. Goldman et al., "Catalytic Alkane Metathesis by Tandem Alkane Dehydrogenation-Olefin Matathesis", Science, vol. 312, Issue 5771, pp. 257-261.

Dong Wang et al., "The Golden Age of Transfer Hydrogenation", Chemical Reviews, 2015, vol. 115, pp. 6621-6686.

\* cited by examiner

INTEGRATED PROCESS FOR PRODUCING OLEFINS FROM ALKANES BY HYDROGEN TRANSFER

FIELD

This application relates to transfer hydrogenation between light alkanes and olefins, and, more particularly, embodiments related to an integrated olefin production system and process which can produce higher carbon number olefins from corresponding alkanes.

BACKGROUND

In steam cracking, a feedstock is thermally cracked in the presence of high-temperature steam to produce olefins. Suitable feedstocks may include naphtha, liquefied petroleum gas, ethane, propane, or butane, among others. Steam crackers may be integrated into a refinery and therefore can primarily utilize naphtha as a feedstock. With recent advances in hydraulic fracturing and horizontal drilling, there has been a significant increase in availability of light hydrocarbons such as methane, ethane, and propane from unconventional shale sources. These lighter hydrocarbons are often less expensive than refinery naphtha leading to some steam crackers units being switched from refinery naphtha to ethane as a feedstock. Additional on-purpose ethane crackers are being built in the United States gulf coast region to take advantage of abundant ethane feedstocks. However, feedstock changes to steam cracking units may constrain the supply of other olefins product streams such as propylene, butadiene, piperylenes, and cyclopentadiene, which may be utilized within the refinery or be sold as product. These and other product streams may be co-products of naphtha steam cracking which may not present in steam cracking of ethane. Consequently, alternative on-purpose routes of making these olefin product streams have been developed such as catalytic propane dehydrogenation (PDH) to propylene, iso-butane dehydrogenation to iso-butylene, butene oxidative dehydrogenation to butadiene, among others.

Oftentimes, a main product stream from a refinery may be fuels such as automotive fuel gasoline, jet fuel, kerosene, diesel, and marine fuel. Production of fuels oftentimes relies on an interconnected refining process where products from one unit may be used as a feedstock for a downstream unit. There may be technical constraints placed on fuels such as gasoline Reid vapor pressure (RVP) that limits the amount of butanes and pentane that can be blended in motor gasoline. The technical constraints of fuels may lead to a supply glut of the previously mentioned alkanes and olefins as they may be redirected from downstream units to be used as gasoline blend stock. The on-purpose routes to generate C3-C5 olefins from the corresponding alkanes such as dehydrogenation and steam cracking are often energy intensive and may lead to relatively higher cost for the olefin product stream than naphtha steam cracking.

SUMMARY

This application relates to transfer hydrogenation between light alkanes and olefins, and, more particularly, embodiments related to an integrated olefin production system and process which can produce higher carbon number olefins from corresponding alkanes.

Disclosed herein is an example method that includes introducing an ethane feed stream to an ethylene generation unit, the ethane feed stream including ethane. The method further may include generating at least an ethylene effluent stream from the ethylene generation unit, the ethylene effluent stream including ethylene and an unreacted portion of the ethane. The method further may include removing at least a portion of the ethylene effluent stream as an ethylene slip stream. The method further may include introducing at least the ethylene slip stream and an alkane stream including at least one alkane to a hydrogen transfer unit, wherein the hydrogen transfer unit includes at least one bimetallic catalyst including platinum. The method further may include reacting at least a portion of the ethylene and the at least one alkane via transfer hydrogenation to produce at least a mixed product stream including generated ethane from at least a portion of the ethylene, unreacted ethylene, and an olefin corresponding to the at least one alkane. The method further may include introducing at least a portion of the mixed product stream to a product fractionation unit to separate the mixed product stream into at least an ethylene recycle stream including at least a portion of the generated ethane and at least a portion of the unreacted ethylene and a product stream including at least a portion of the olefin corresponding to the at least one alkane. The method further may include recycling at least a portion of the ethane recycle stream to the ethylene generation unit.

Further disclosed herein is another method that may include introducing ethylene and propane into a hydrogen transfer unit, wherein the ethylene is provided by an ethylene generation unit. The hydrogen transfer unit may include at least one bimetallic catalyst that includes platinum. The method may further include reacting at least the ethylene and the propane via transfer hydrogenation to generate ethane and propylene, wherein the transfer hydrogenation occurs at a temperature less than about 400° C. and a pressure greater than about 1380 kPa. The method may further include separating the ethane and propylene. The method may further include recycling at least a portion of the ethane, wherein the portion of the ethane is recycled to the ethylene generation unit.

Further disclosed herein is an example system that may include an ethane cracking unit. The example system may further include a hydrogen transfer unit, wherein an effluent stream from the ethane cracking unit and an alkane stream are coupled to one or more inputs of the hydrogen transfer unit, wherein the hydrogen transfer unit includes at least one bimetallic catalyst including platinum. The example system may further include a product fractionation unit, wherein an output stream of the hydrogen transfer unit is coupled to an input of the product fractionation unit; and wherein an overhead stream from the product fractionation unit is coupled to an input of the ethane cracking unit.

BRIEF DESCRIPTION OF THE DRAWINGS

These drawings illustrate certain aspects of the present invention and should not be used to limit or define the invention.

DETAILED DESCRIPTION

Figure 1:
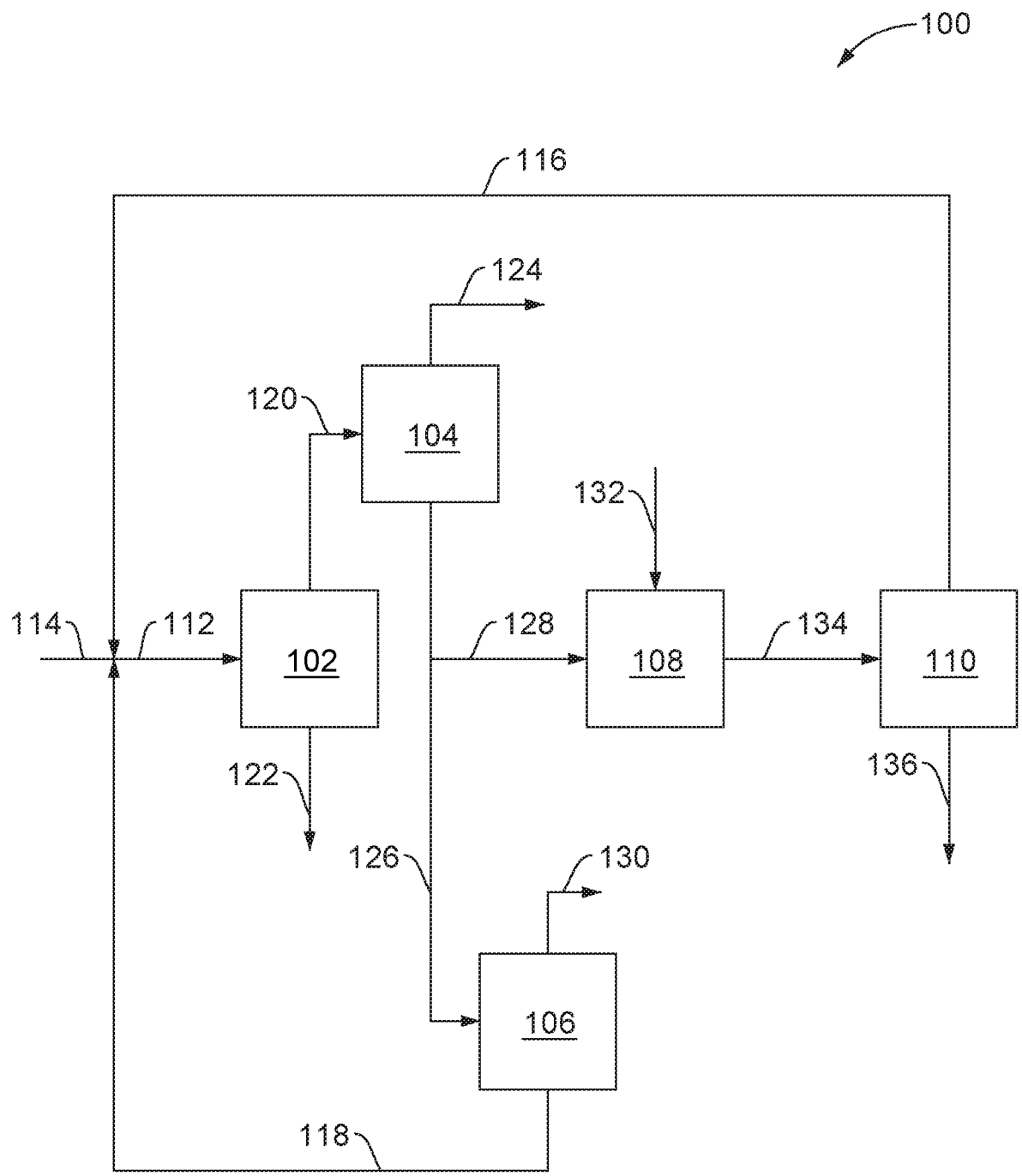
FIG. 1. is a schematic diagram illustrating an embodiment of an integrated transfer hydrogenation process.

This application relates to transfer hydrogenation between light alkanes and olefins, and, more particularly, embodiments related to an integrated olefin production system and process which can produce higher carbon number olefins from corresponding alkanes while converting ethylene to ethane. While the methods and systems disclose herein may be suitable to provide olefins in a standalone unit, the methods and systems may be particularly suitable for an integrated process within a refinery.

There may be several potential advantages to the methods and systems disclosed herein, only some of which may be alluded to in the present disclosure. One of the many potential advantages of the methods and systems is that the inefficiencies from utilizing on-purpose olefin production and separation methods may be addressed. As discussed above, steam cracking and dehydrogenation may be two processes which produce on-purpose olefins. Catalytic alkane dehydrogenation to produce olefins typically requires high temperatures, low pressure, and frequent catalyst regeneration. Dehydrogenation methods may be limited by low equilibrium conversions due to the endothermic nature of the dehydrogenation reactions. The relatively low-per pass conversion in dehydrogenation methods may lead to a large recycle ratio. Steam cracking of naphtha and alkanes to produce olefins also requires high temperatures, low alkane partial pressure, and the reactor may be readily fouled by coking reactions. In either process, process conditions which favor olefin production are high temperature (e.g., >840° F. or 450° C.) and low pressure (ambient or vacuum). These process conditions are often satisfied by supplying large amounts of heat to the reactor to overcome the equilibrium constraint to reach appreciable per-pass olefin conversion. Products of dehydrogenation and steam cracking often require cryogenic separation and compression which adds to the energy requirement of the alkane-to-olefins conversion process. In a typical steam cracker, olefins production accounts for approximately one-third of the overall unit operational cost, and olefins separation accounts for approximately two-thirds of the overall unit operational cost.

The methods and systems described herein may utilize transfer hydrogenation to reduce process severity and energy requirement of olefin production. Transfer hydrogenation may be described as transferring a hydrogen molecule ($H_2$) from a first alkane to a first olefin, thereby producing a second olefin corresponding to the first alkane and a second alkane corresponding to the first olefin. The process may be utilized to convert higher carbon number alkanes, such as C3-C5, to the corresponding olefins while converting another lower carbon number olefin such as ethylene to ethane. The ethane may be separated and recycled to an integrated ethane to ethylene process whereby ethane may be converted to ethylene. The produced ethylene from transfer hydrogenation may be integrated alongside ethane-to-ethylene processes such as ethane steam cracking, ethane oxidative dehydrogenation, ethane catalytic dehydrogenation, metal oxide looping, or a combination thereof. The integrated transfer hydrogenation/ethane-to-ethylene process may produce both low carbon number and high carbon number olefins from an alkane feedstock with lower energy requirements than separate steam cracking or dehydrogenation steps for each olefin.

Transfer hydrogenation is a near thermoneutral process, and the enthalpy change associated with embodiments of the transfer of hydrogen from a higher carbon number alkane to a lower carbon number is significantly lower than dehydrogenation methods. As such embodiments of the hydrogen transfer can be nearly enthalpy-neutral and the reaction should not be constrained by equilibrium conversion to the extent that dehydrogenation methods are. In the transfer hydrogenation reaction, there should be little to no volume expansion as the relative number of gas molecules should remain unchanged, which allows for the reaction to be run at higher pressure, increasing mass flow rate of feedstock and reducing overall reactor size.

FIG. 1 illustrates an embodiment of an integrated transfer hydrogenation process 100. As illustrated, integrated transfer hydrogenation process 100 may include ethylene unit 102, hydrogen separation unit 104, C2 splitter unit 106, hydrogen transfer unit 108, and production fractionation unit 110. Integrated transfer hydrogenation process 100 may begin with generation of ethylene in ethylene unit 102. Ethylene unit 102 may be any suitable ethylene production unit such as a steam cracker or dehydrogenation unit, for example. Ethylene unit 102 may take feed gas stream 112 and produce cracked gas stream 120 and bottoms stream 122.

Feed gas stream 112 may be any suitable source of ethane. As illustrated, feed gas stream 112 may be a mixture of ethane recycle stream 116, ethane bottoms stream 118, and makeup ethane stream 114. Feed gas stream 112 may include ethane as the major species with minor to no amounts of methane, ethylene, and propane depending on downstream process conditions and composition of makeup ethane stream 114. While ethane recycle stream 116, ethane bottoms stream 118, and makeup ethane stream 114 are shown being mixed prior to ethylene unit 102, one or more of these streams may also be separately introduced to ethylene unit 102. In embodiments where ethylene unit 102 is a steam cracker, a steam feed (not shown) may also be fed into ethylene unit 102. Ethylene unit 102 may crack or catalytically dehydrogenate ethane in feed gas stream 112 to produce cracked gas stream 120, which may include ethylene, ethane, and hydrogen, for example. Selectivity to ethylene may be high within ethylene unit 102 with a trace amount of species heavier than ethane being produced. Conversion of ethane to ethylene within ethylene unit 102 may be about 80-85 wt. % depending on unit type and operating conditions, for example. There may be many unit operations within an ethylene unit not specifically discussed herein that occur after the step of cracking or catalytically dehydrogenating feed gas stream 112. Cracked gas stream 120 may be drawn from any suitable location within an ethylene unit, the location of which may vary from one ethylene unit to another. Ethylene unit 102 is merely illustrative of one embodiment of an ethylene unit and one of ordinary skill in the art should be able to readily recognize an appropriate location within ethylene unit 102 from which to draw cracked gas stream 120. Similarly, bottoms stream 122 is a generalized bottoms stream from ethylene unit 102 illustrating some potential bottoms products generated during cracking or catalytically dehydrogenating feed gas stream 112. Bottoms stream 122 may include products heavier than ethane, including, but not limited to, quench tower blowdown, tar, oil, propane, propylene, and benzene, for example.

Ethylene unit 102 may operate at any suitable pressure and temperature for ethylene production. Reaction conditions in ethylene unit 102 may vary depending on many factors including whether ethylene unit 102 is a steam cracker or dehydrogenation unit and the type of catalyst present in the reactor vessel, for example. In general, pressure within a reactor vessel in ethylene unit 102 may range from about vacuum (0 kPa) to about 200 kPa. In general, temperature within a reactor vessel in ethylene unit 102 may range from about 930° F. (500° C.) to about 1830° F. (1000° C.). In addition to reactors, there may be additional equipment and unit operations performed within ethylene unit 102 not explicitly depicted in FIG. 1, such as, without limitation, quenching equipment, compressors, caustic treatment equipment, acetylene hydrogenation equipment, and distillation equipment, for example.

From ethylene unit 102, cracked gas stream 120 may be transported to hydrogen separation unit 104. Hydrogen separation unit 104 may include any suitable hydrogen separation process such as, without limitation, membrane permeation, pressure swing adsorption, or cryogenic distillation within a cold box, for example. In hydrogen separation unit 104, hydrogen may be separated from ethane and ethylene to produce hydrogen stream 124 containing at least a portion of the hydrogen from cracked gas stream 120 and C2 stream 126 containing the ethane and ethylene from cracked gas stream 120. For example, substantially all of the hydrogen may be separated from cracked gas stream 120 in hydrogen separation unit 104. In some embodiments, hydrogen stream 124 may contain about 90 wt. %, about 95 wt. %, about 98 wt. %, about 99 wt. %, or more of the hydrogen from cracked gas stream 120. In some embodiments, hydrogen separation unit 104 may be integrated into ethylene unit 102 as part of one or more unit operations. C2 stream 126 from hydrogen separation unit 104 may be split into C2 side stream 128 and sent to hydrogen transfer unit 108. The balance of C2 stream 126 not split to C2 side stream 128 may be sent to C2 splitter unit 106. Any suitable split amount of C2 stream 126 may be split into C2 side stream 128 and sent to hydrogen transfer unit 108. For example, C2 side stream 128 may contain about 1% to about 100% of the mass from C2 stream 126. Alternatively, C2 side stream 128 may contain about 1% to about 20% of the mass from C2 stream 126, about 20% to about 40% of the mass from C2 stream 126, about 40% to about 60% of the mass from C2 stream 126, about 60% to about 80% of the mass from C2 stream 126, or about 80% to about 100% of the mass from C2 stream 126.

In C2 splitter unit 106, ethylene and ethane in C2 stream 126 may be separated into ethylene product stream 130 and ethane bottoms stream 118. Ethane bottoms stream 118 may be recycled to be mixed with ethane recycle stream 116 and make up ethane stream 114 to produce feed gas stream 112 as previously discussed. Ethylene product stream 130 may contain the balance of ethylene from C2 stream 126. Ethylene product stream 130 may be made to any ethylene purity desired such as pipeline grade, refinery grade, or polymer grade ethylene based on separation methodology. C2 splitter unit 106 may utilize any separation methodology such as, without limitation, cryogenic distillation, molecular sieve separation such as $Ag^+$ or $Cu^+$ doped molecular sieves, or ion-facilitated membrane separation, for example. In some embodiments, C2 splitter unit 106, may be integrated into ethylene unit 102 as part of one or more unit operations.

From hydrogen separation unit 104, C2 side stream 128 containing ethane and ethylene may be introduced into hydrogen transfer unit 108 alongside alkane stream 132. Hydrogen transfer unit 108 may take alkane stream 132 and mixed product stream 134. Alkane stream 132 may include an alkane desired to be converted to an olefin. As discussed above, the transfer hydrogenation process may remove an $H_2$ molecule from a first alkane and transfer the $H_2$ molecule to a first olefin thereby producing a second olefin from the first alkane and a second alkane from the first olefin. In at least one embodiment, the first alkane may have a higher carbon number than the first olefin to facilitate the transfer hydrogenation reaction proceeding in the desired direction. The transfer hydrogenation reaction may be thermodynamically favored to proceed to hydrogenating the smaller carbon number olefin as the second and higher carbon number olefin produced during the hydrogen transfer reaction may be more stable than the first olefin. Without being limited by theory, the first alkane may be any length alkane that is desired to be converted to an olefin. For example, the first alkane may be butane which would be converted to butenes such as 1-butene, cis-2-butene, trans-2-butene, and 1,2-butadiene. Alternatively, the first alkane may be any of propane, butane and isomers thereof, pentane and isomers thereof, cyclopentane, hexane and isomers thereof, and cyclohexane. Each of the alkanes should produce the corresponding olefin or mixtures of olefins in the transfer hydrogenation reaction. Selectivity to particular olefins may be controlled by catalyst selection and catalyst tuning and to a lesser extent, process conditions such as pressure and temperature.

Alkane stream 132 may include one or more alkanes such as, without limitation, propane, butane, pentane, hexane, any isomers thereof, or any combinations thereof. Hydrogen transfer unit 108 may include a reactor vessel with a transfer hydrogenation catalyst disposed therein as well as auxiliary reactor equipment such as reactor control systems and process equipment required to control the transfer hydrogenation reaction. In hydrogen transfer unit 108, ethylene from C2 side stream 128 and the one or more alkanes from alkane stream 132 may be introduced into the reactor vessel and brought in contact with the transfer hydrogenation catalyst to facilitate the transfer hydrogenation reaction. Ethylene may act as a hydrogen acceptor and a hydrogen may be transferred from the one or more alkanes to the ethylene to produce ethane and an olefin product corresponding to the one or more alkanes. The molar ratio of ethylene to alkane introduced into hydrogen transfer unit 108 may be varied to achieve desired hydrogen transfer. For example, the molar ratio of ethylene to alkane may range from about 1:10, 1:5, 1:3, 1:2, 1:1, 2:1, 3:1, 5:1, 10; 1 or even higher.

Mixed product stream 134 from hydrogen transfer unit 108 may include ethane, unreacted ethylene, unreacted alkane, and olefin product. Mixed product stream 134 may be introduced into product fractionation unit 110 whereby the components of mixed product stream 134 may be separated. Ethylene and ethane in mixed product stream 134 may be separated from the unreacted alkane and olefin product as ethane recycle stream 116. Ethane recycle stream 116 may be transported to and mixed with ethane bottoms stream 118 and make up ethane stream 114 to produce feed gas stream 112 as previously discussed. Olefin product stream 136 may include the unreacted alkane and olefin product from mixed product stream 134. Product fractionation unit 110 may utilize any separation methodology such as, without limitation, cryogenic distillation, molecular sieve separation such as $Ag^+$ or $Cu^+$ doped molecular sieves, or ion-facilitated membrane separation, for example. In some embodiments, product fractionation unit 110 may further separate unreacted alkane from olefin product and generate an unreacted alkane recycle stream which may be recycled to alkane stream 132, and a purified olefin product stream.

The reactor vessel of hydrogen transfer unit 108 may operate at any temperature and pressure conditions suitable to allow the transfer hydrogenation reaction between ethylene from C2 side stream 128 and the one or more alkanes from alkane stream 132 to take place. For example, the reactor vessel of hydrogen transfer unit 108 may be operated at a temperature ranging from about 32° F. (0° C.) to about 1110° F. (600° C.). Alternatively, the reactor vessel may be operated at a temperature ranging from about 32° F. (0° C.) to about 100° F. (38° C.), about 100° F. (38° C.) to about 200° F. (93° C.), about 200° F. (93° C.) to about 300° F. (149° C.), about 300° F. (149° C.) to about 400° F. (204° C.), about 400° F. (204° C.) to about 500° F. (260° C.), about 500° F. (206° C.) to about 600° F. (316° C.), about 600° F. (316° C.) to about 700° F. (371° C.), about 700° F. (371° C.) to about 800° F. (427° C.), about 800° F. (427° C.) to about 900° F. (482° C.), about 900° F. (482° C.) to about 1000° F. (538° C.), or about 1000° F. (538° C.) to about 1110° F. (599° C.). The reactor vessel of hydrogen transfer unit 108 may operate at any pressure ranging from about atmospheric (14.7 psi 101.325 kPa) to about 1400 psi (6952 kPa). Alternatively, the reactor vessel may operate at a pressure ranging from about 14.7 psi (101.325 kPa) to about 250 psi (1725 kPa), about 250 psi (1725 kPa) to about 500 psi (3447 kPa), about 500 psi (3447 kPa) to about 750 psi (5171 kPa), about 750 psi (5171 kPa) to about 1000 psi (6895 kPa), about 1000 psi (6895 kPa) to about 1200 psi (8274 kPa), or about 1200 psi (8274 kPa) to about 1400 psi (9653 kPa). The catalyst present in the reactor vessel of hydrogen transfer unit 108 may a bimetallic catalyst that includes platinum and that facilitates the transfer hydrogenation reaction between ethylene from C2 side stream 128 and the one or more alkanes from alkane stream 132. Suitable examples of suitable bimetallic catalyst may include platinum/tin, platinum/gallium, or platinum/rhenium systems. The catalysts may include a support, such as zeolite, alumina, or silica for example, to which the catalytic metals may be attached.

The catalyst and process conditions may be selected such that the production of methane in the hydrogen transfer process is minimized Production of methane is generally undesired as a portion of the alkane stream is wasted and the product methane may be required to be removed before the olefin products are utilized in downstream processes. Bimetallic catalysts, a relatively lower reaction temperature of 550° F. (288° C.) to 850° F. (455) ° C., and a relatively higher reaction pressure of 345 kPa may promote the formation of olefins while reducing the production of methane. Furthermore, selection of a bimetallic catalyst and process conditions which suppress methane forming reactions may eliminate catalyst pretreatment steps typically utilized to suppress methane formation. For example, the pretreatment of the catalyst may be heating of the catalyst to an elevated temperature (e.g., about 200° C. or greater or about 450° C. or greater). This pretreatment may also be performed immediately prior to use (e.g., within about 4 hours or less). In some examples, conversion of the alkane stream to methane may be 1% or less. Alternatively, the conversion of the alkane stream may be 0.5% or less, 0.1% or less, or 0% conversion.

Accordingly, the preceding description describes transfer hydrogenation of light alkanes. The systems and methods disclosed herein may include any of the various features disclosed herein, including one or more of the following embodiments.

Embodiment 1. A method comprising: introducing an ethane feed stream to an ethylene generation unit, the ethane feed stream comprising ethane; generating at least an ethylene effluent stream from the ethylene generation unit, the ethylene effluent stream comprising ethylene and an unreacted portion of the ethane; removing at least a portion of the ethylene effluent stream as an ethylene slip stream; introducing at least the ethylene slip stream and an alkane stream comprising at least one alkane to a hydrogen transfer unit, wherein the hydrogen transfer unit comprises at least one bimetallic catalyst comprising platinum; reacting at least a portion of the ethylene and the at least one alkane via transfer hydrogenation to produce at least a mixed product stream comprising generated ethane from at least a portion of the ethylene, unreacted ethylene, and an olefin corresponding to the at least one alkane; introducing at least a portion of the mixed product stream to a product fractionation unit to separate the mixed product stream into at least an ethylene recycle stream comprising at least a portion of the generated ethane and at least a portion of the unreacted ethylene and a product stream comprising at least a portion of the olefin corresponding to the at least one alkane; and recycling at least a portion of the ethylene recycle stream to the ethylene generation unit.

Embodiment 2. The method of embodiment 1 wherein the ethylene generation unit comprises an ethane steam cracker or an ethane dehydrogenation reactor.

Embodiment 3. The method of any of embodiments 1-2 wherein the ethylene effluent stream further comprises hydrogen, and wherein the method further comprises: introducing the ethylene effluent stream to a hydrogen separation unit before the step of separating a portion of the ethylene effluent stream as an ethylene slip stream; and separating a substantial portion of the hydrogen from the ethylene effluent stream.

Embodiment 4. The method of embodiment 3 wherein the hydrogen separation unit comprises at least one of membrane permeation, pressure swing adsorption, or cryogenic distillation within a cold box.

Embodiment 5. The method of any of embodiments 1-4 wherein the at least one alkane comprises at least one alkane selected from the group consisting of propane, butane, pentane, hexane, any isomers thereof, or any combinations thereof.

Embodiment 6. The method of any of embodiments 1-5 wherein the hydrogen transfer unit operates at a temperature of about 0° C. to about to about 500° C. and a pressure of about 100 kPa to about 1725 kPa.

Embodiment 7. The method of any of embodiments 1-6 wherein less than 1% of the at least one alkane is converted to methane.

Embodiment 8. The method of any of embodiments 1-7 wherein a mole ratio of the ethylene to alkane introduced into the hydrogen transfer unit is about 1:10 to about 10:1.

Embodiment 9. The method of any of embodiments 1-8 wherein the bimetallic catalyst further comprises at least one additional metal selected from the group consisting of tin, gallium, and rhenium.

Embodiment 10. The method of any of embodiments 1-9 further comprising: introducing at least a portion the ethylene effluent stream into a C2 splitter unit; generating an ethylene bottoms stream comprising at least a portion the ethane from the ethylene effluent stream and an ethylene product stream comprising at least a portion of the ethylene from the ethylene effluent stream; and recycling at least a portion of the ethylene bottoms stream to the ethylene generation unit.

Embodiment 11 A method comprising: introducing ethylene and propane into a hydrogen transfer unit, wherein the ethylene is provided by an ethylene generation unit, wherein the the hydrogen transfer unit comprises at least one bimetallic catalyst comprising platinum; reacting at least the ethylene and the propane via transfer hydrogenation to generate ethane and propylene, wherein the transfer hydrogenation occurs at a temperature less than about 400° C. and a pressure greater than about 1380 kPa; separating at least a portion of the ethane from the propylene; and recycling at least a portion of the ethane, wherein the portion of the ethane is recycled to the ethylene generation unit.

Embodiment 12. The method of embodiment 11 wherein a mole ratio of the ethylene to propane introduced into the hydrogen transfer unit is about 10:1 to about 1:10.

Embodiment 13. The method of any of embodiments 11-12 wherein the bimetallic catalyst further comprises at least one additional metal selected from the group consisting of tin, gallium, and rhenium.

Embodiment 14. The method of any of embodiments 11-13 wherein less than 1% of the propane is converted to methane.

Embodiment 15. A system comprising: an ethane cracking unit; a hydrogen transfer unit, wherein an effluent stream from the ethane cracking unit and an alkane stream are coupled to one or more inputs of the hydrogen transfer unit, wherein the hydrogen transfer unit comprises at least one bimetallic catalyst comprising platinum; a product fractionation unit, wherein an output stream of the hydrogen transfer unit is coupled to an input of the product fractionation unit; and wherein an overhead stream from the product fractionation unit is coupled to an input of the ethane cracking unit.

Embodiment 16. The system of embodiment 15 wherein the hydrogen transfer unit comprises a reactor containing the bimetallic catalyst.

Embodiment 17. The system of embodiment 16 wherein the reactor is configured to operate at a temperature less than about 500° C. and a pressure greater than about 1380 kPa.

Embodiment 18. The system of any of embodiments 15-17 wherein the bimetallic catalyst further comprises at least one additional metal selected from the group consisting of tin, gallium, and rhenium.

Embodiment 19. The system of any of embodiments 15-18 further comprising: a hydrogen separation unit, wherein the effluent stream from the ethane cracking unit is coupled to an input of the hydrogen separation unit, and wherein the hydrogen separation unit is placed between the ethane cracking unit and the hydrogen transfer unit.

Embodiment 20. The system of any of embodiments 15-19 further comprising: a C2 splitter, wherein a portion of the effluent stream from the ethane cracking unit is directed to an input of the C2 splitter, and wherein a bottom stream from the C2 splitter is coupled to the input of the ethane cracking unit.

EXAMPLES

To facilitate a better understanding of the present invention, the following examples of certain aspects of some embodiments are given. In no way should the following examples be read to limit, or define, the entire scope of the invention.

Example 1

Figure 2A:
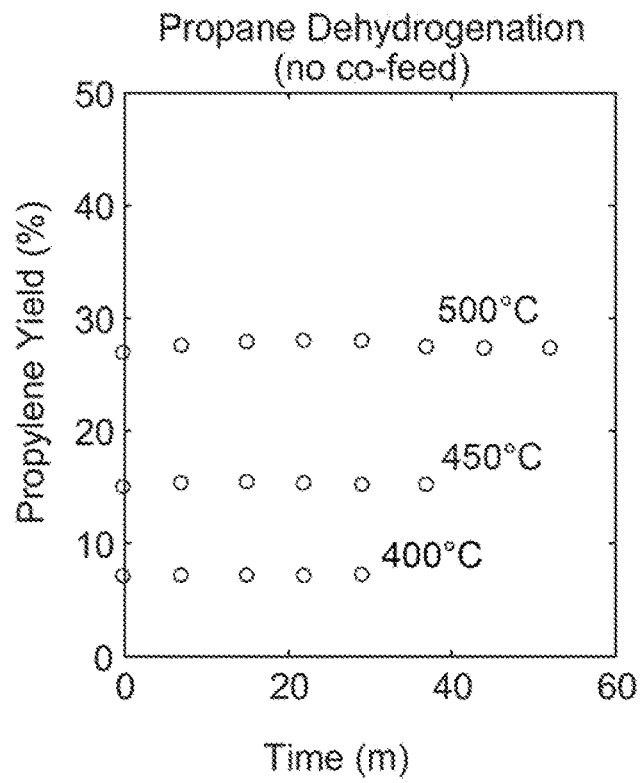
FIG. 2A is a graph showing results of a dehydrogenation experiment.

In this example, conversion of propane to propylene under 0 psig (101.235 kPa absolute) via catalytic propane dehydrogenation was tested. The reactor was a single pass fixed bed reactor with Pt/Sn bimetallic catalyst. The tests were run at 400° C., 450° C., and 500° C. Propylene was charged to the reactor and the reaction was run with a weighted hourly space velocity (WHSV) of 4 g/g/hr. The composition of the reactor effluent was monitored, and results are shown in Table 1. The data from Table 1 is graphed in FIG. 2A. It was observed that the yield of propylene and methane both increased with increasing temperature.

TABLE 1

| Time (m) | Propylene Yield (%) | Methane Yield (%) | Temperature (° C.) |
|---|---|---|---|
| 0 | 7.1 | 0.1% | 400 |
| 7 | 7.1 | 0.1% | 400 |
| 15 | 7.1 | 0.1% | 400 |
| 22 | 7.1 | 0.1% | 400 |
| 29 | 7.2 | 0.1% | 400 |
| 0 | 15.0 | 0.4% | 450 |
| 7 | 15.3 | 0.5% | 450 |
| 15 | 15.4 | 0.5% | 450 |
| 22 | 15.3 | 0.5% | 450 |
| 29 | 15.2 | 0.5% | 450 |
| 37 | 15.2 | 0.5% | 450 |
| 0 | 26.9 | 1.1% | 500 |
| 7 | 27.5 | 1.2% | 500 |
| 15 | 27.9 | 1.2% | 500 |
| 22 | 28.0 | 1.3% | 500 |
| 29 | 28.0 | 1.3% | 500 |
| 37 | 27.4 | 1.2% | 500 |
| 44 | 27.3 | 1.2% | 500 |
| 52 | 27.3 | 1.2% | 500 |

Example 2

Figure 2B:
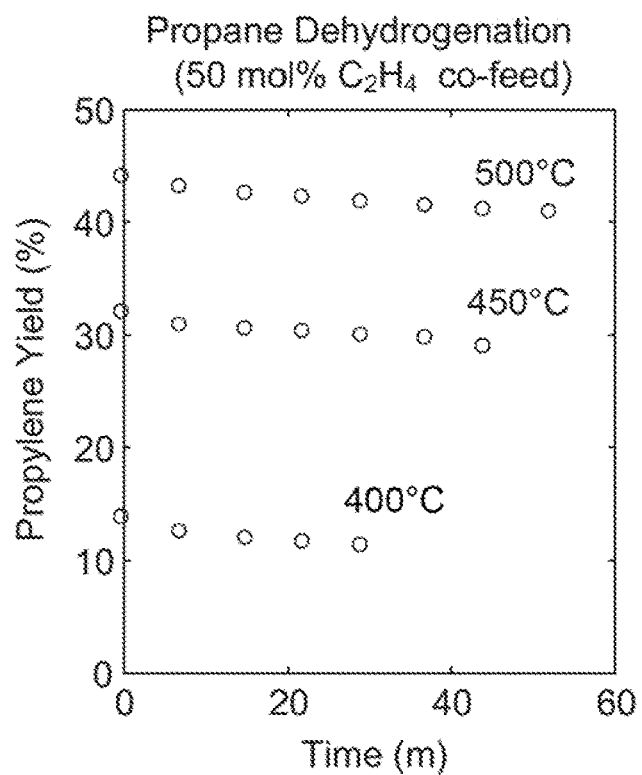
FIG. 2B is a graph showing results of a hydrogen transfer experiment.

In this example, conversion of propane to propylene under 0 psig (101.235 kPa absolute) via hydrogen transfer was tested. The same reactor configuration and catalyst from Example 1 was used. Propane and an ethylene co-feed were charged to the reactor and the reaction was run with a WHSV of 4 g/g/hr. The tests were run at 400° C., 450° C., and 500° C. The composition of the reactor effluent was monitored, and results are shown in Table 2. The data from Table 2 is graphed in FIG. 2B. It was observed that the yield of propylene and methane both increased with increasing temperature, but the yield of methane is lower at all temperatures as compared to the results of Example 1.

TABLE 2

| Time (m) | Propylene Yield (%) | Methane Yield (%) | Temperature (° C.) |
|---|---|---|---|
| 0 | 13.9 | 0.0% | 400 |
| 7 | 12.6 | 0.0% | 400 |
| 15 | 12.0 | 0.0% | 400 |
| 22 | 11.7 | 0.0% | 400 |
| 29 | 11.4 | 0.0% | 400 |
| 0 | 32.0 | 0.1% | 450 |
| 7 | 30.9 | 0.1% | 450 |
| 15 | 30.5 | 0.1% | 450 |
| 22 | 30.3 | 0.1% | 450 |
| 29 | 30.0 | 0.0% | 450 |
| 37 | 29.8 | 0.0% | 450 |
| 44 | 29.0 | 0.0% | 450 |
| 0 | 44.0 | 0.5% | 500 |
| 7 | 43.1 | 0.4% | 500 |
| 15 | 42.6 | 0.4% | 500 |
| 22 | 42.2 | 0.4% | 500 |
| 29 | 41.8 | 0.3% | 500 |
| 37 | 41.4 | 0.3% | 500 |
| 44 | 41.1 | 0.3% | 500 |
| 52 | 40.9 | 0.3% | 500 |

Example 3

Figure 3A:
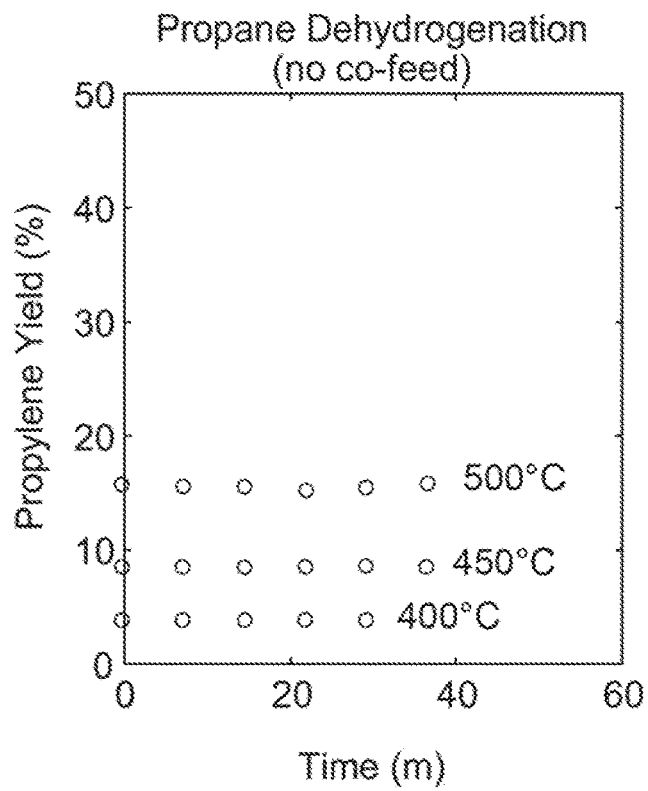
FIG. 3A is a graph showing results of a dehydrogenation experiment.

In this example, conversion of propane to propylene under 50 psig (446 kPa absolute) via catalytic propane dehydrogenation was tested. The same reactor configuration and catalyst from Example 1 was used. The tests were run at 400° C., 450° C., and 500° C. Propylene was charged to the reactor and the reaction was run with a weighted hourly space velocity (WHSV) of 4 g/g/hr. The composition of the reactor effluent was monitored, and results are shown in Table 3. The data from Table 3 is graphed in FIG. 3A. It was observed that the yield of propylene and methane both increased with increasing temperature. The yield of methane at the higher pressure of Example 3 is lower than in the yield of methane of the lower pressures of Example 1 at temperatures greater than 400° C.

TABLE 3

| Time (m) | Propylene Yield (%) | Methane Yield (%) | Temperature (° C.) |
| --- | --- | --- | --- |
| 0 | 3.7 | 0.1% | 400 |
| 7 | 3.7 | 0.1% | 400 |
| 15 | 3.8 | 0.1% | 400 |
| 22 | 3.8 | 0.1% | 400 |
| 29 | 3.8 | 0.1% | 400 |
| 0 | 8.3 | 0.2% | 450 |
| 7 | 8.4 | 0.3% | 450 |
| 15 | 8.4 | 0.3% | 450 |
| 22 | 8.4 | 0.3% | 450 |
| 29 | 8.5 | 0.3% | 450 |
| 37 | 8.4 | 0.3% | 450 |
| 0 | 15.5 | 0.4% | 500 |
| 7 | 15.4 | 0.4% | 500 |
| 15 | 15.4 | 0.4% | 500 |
| 22 | 15.1 | 0.5% | 500 |
| 29 | 15.3 | 0.5% | 500 |
| 37 | 15.6 | 0.5% | 500 |

Example 4

Figure 3B:
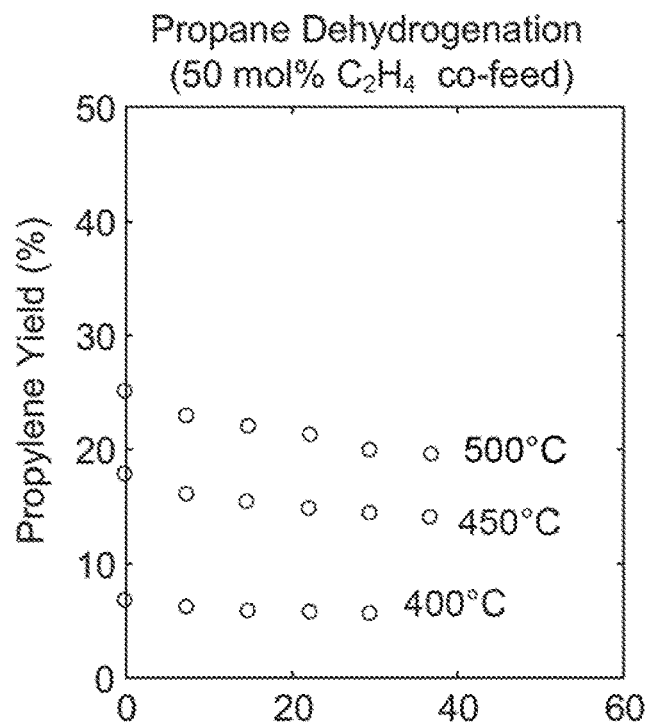
FIG. 3B is a graph showing results of a hydrogen transfer experiment.

In this example, conversion of propane to propylene under 50 psig (446 kPa absolute) via hydrogen transfer was tested. The same reactor configuration and catalyst from Example 1 was used. Propane and an ethylene co-feed were charged to the reactor and the reaction was run with a WHSV of 4 g/g/hr. The tests were run at 400° C., 450° C., and 500° C. The composition of the reactor effluent was monitored, and results are shown in Table 4. The data from Table 4 is graphed in FIG. 3B. It was observed that the yield of propylene and methane both increased with increasing temperature, but the yield of methane is lower at all temperatures as compared to the results of any of the previous experiments.

TABLE 4

| Time (m) | Propylene Yield (%) | Methane Yield (%) | Temperature (° C.) |
| --- | --- | --- | --- |
| 0 | 6.7 | 0.0% | 400 |
| 7 | 6.1 | 0.0% | 400 |
| 15 | 5.8 | 0.0% | 400 |
| 22 | 5.7 | 0.0% | 400 |
| 29 | 5.5 | 0.0% | 400 |
| 0 | 17.8 | 0.0% | 450 |
| 7 | 16.0 | 0.0% | 450 |
| 15 | 15.3 | 0.0% | 450 |
| 22 | 14.7 | 0.0% | 450 |
| 29 | 14.3 | 0.0% | 450 |
| 37 | 14.0 | 0.0% | 450 |
| 0 | 25.0 | 0.1% | 500 |
| 7 | 22.8 | 0.1% | 500 |
| 15 | 21.9 | 0.1% | 500 |
| 22 | 21.1 | 0.1% | 500 |
| 29 | 19.8 | 0.1% | 500 |
| 37 | 19.4 | 0.1% | 500 |

While the invention has been described with respect to a number of embodiments and examples, those skilled in the art, having benefit of this disclosure, will appreciate that other embodiments can be devised which do not depart from the scope and spirit of the invention as disclosed herein. Although individual embodiments are discussed, the invention covers all combinations of all those embodiments.

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used.

All numerical values within the detailed description and the claims herein modified by "about" or "approximately" with respect the indicated value are intended to take into account experimental error and variations that would be expected by a person having ordinary skill in the art.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

The invention claimed is:

1. A method comprising:
introducing an ethane feed stream to an ethylene generation unit, the ethane feed stream comprising ethane;
generating at least an ethylene effluent stream from the ethylene generation unit, the ethylene effluent stream comprising ethylene and an unreacted portion of the ethane;
splitting at least a portion of the ethylene effluent stream into a first ethylene effluent stream and a second ethylene effluent stream;
introducing at least the first ethylene effluent stream and an alkane stream comprising at least one alkane to a hydrogen transfer unit, wherein the hydrogen transfer unit comprises at least one bimetallic catalyst comprising platinum;
reacting at least a portion of the ethylene from the first ethylene effluent stream and the at least one alkane via transfer hydrogenation in the hydrogen transfer unit to produce at least a mixed product stream comprising generated ethane from at least a portion of the ethylene, unreacted ethylene, and an olefin corresponding to the at least one alkane;

introducing at least a portion of the mixed product stream to a product fractionation unit to separate the mixed product stream into at least an ethylene recycle stream comprising at least a portion of the generated ethane and at least a portion of the unreacted ethylene and a product stream comprising at least a portion of the olefin corresponding to the at least one alkane;

recycling at least a portion of the ethylene recycle stream to the ethylene generation unit;

introducing the second ethylene effluent stream into a C2 splitter unit;

generating an ethylene bottoms stream comprising at least a portion of the ethane from the ethylene effluent stream and an ethylene product stream comprising at least a portion of the ethylene from the ethylene effluent stream; and recycling at least a portion of the ethylene bottoms stream to the ethylene generation unit.

2. The method of claim 1 wherein the ethylene generation unit comprises an ethane steam cracker or an ethane dehydrogenation reactor.

3. The method of claim 1 wherein the ethylene effluent stream further comprises hydrogen, and wherein the method further comprises:

introducing the ethylene effluent stream to a hydrogen separation unit before the step of splitting at least a portion of the ethylene effluent stream into a first ethylene effluent stream and a second ethylene effluent stream; and separating a substantial portion of the hydrogen from the ethylene effluent stream.

4. The method of claim 3 wherein the hydrogen separation unit comprises at least one of membrane permeation, pressure swing adsorption, or cryogenic distillation within a cold box.

5. The method of claim 1 wherein the at least one alkane comprises at least one alkane selected from the group consisting of propane, butane, pentane, hexane, any isomers thereof, or any combinations thereof.

6. The method of claim 1 wherein the hydrogen transfer unit operates at a temperature of about 0° C. to about to about 500° C. and a pressure of about 100 kPa absolute to about 1725 kPa absolute.

7. The method of claim 1 wherein less than 1% of the at least one alkane is converted to methane.

8. The method of claim 1 wherein a mole ratio of the ethylene to alkane introduced into the hydrogen transfer unit is about 1:10 to about 10:1.

9. The method of claim 1 wherein the bimetallic catalyst further comprises at least one additional metal selected from the group consisting of tin, gallium, and rhenium.

10. A method comprising:

introducing an ethane feed stream to an ethylene generation unit, the ethane feed stream comprising ethane;

generating at least an ethylene effluent stream from the ethylene generation unit, the ethylene effluent stream comprising ethylene and an unreacted portion of the ethane;

splitting at least a portion of the ethylene effluent stream into a first ethylene effluent stream and a second ethylene effluent stream;

introducing the first ethylene effluent stream and a propane stream comprising propane into a hydrogen transfer unit, wherein the hydrogen transfer unit comprises at least one bimetallic catalyst comprising platinum;

reacting at least a portion of the ethylene from the first ethylene effluent stream and the propane via transfer hydrogenation in the hydrogen transfer unit to generate ethane and propylene, wherein the transfer hydrogenation occurs at a temperature less than about 400° C. and a pressure greater than about 1380 kPa absolute;

separating at least a portion of the generated ethane from the propylene;

recycling at least a portion of the separated ethane to the ethylene generation unit;

introducing the second ethylene effluent stream into a C2 splitter unit;

generating an ethylene bottoms stream comprising at least a portion of the ethane from the ethylene effluent stream and an ethylene product stream comprising at least a portion of the ethylene from the ethylene effluent stream; and recycling at least a portion of the ethylene bottoms stream to the ethylene generation unit.

11. The method of claim 10 wherein a mole ratio of the ethylene to propane introduced into the hydrogen transfer unit is about 10:1 to about 1:10.

12. The method of claim 10 wherein the bimetallic catalyst further comprises at least one additional metal selected from the group consisting of tin, gallium, and rhenium.

13. The method of claim 10 wherein less than 1% of the propane is converted to methane.

* * * * *